US011517432B2

(12) United States Patent
Costello

(10) Patent No.: US 11,517,432 B2
(45) Date of Patent: Dec. 6, 2022

(54) EXPANDABLE INTRODUCER SHEATH

(71) Applicant: Medtronic Vascular, Inc., Santa Rosa, CA (US)

(72) Inventor: Declan Costello, Ballybrit (IE)

(73) Assignee: Medtronic Vascular, Inc., Santa Rosa, CA (US)

( * ) Notice: Subject to any disclaimer, the term of this patent is extended or adjusted under 35 U.S.C. 154(b) by 59 days.

(21) Appl. No.: 16/822,658

(22) Filed: Mar. 18, 2020

(65) Prior Publication Data

US 2020/0214839 A1 Jul. 9, 2020

Related U.S. Application Data

(63) Continuation of application No. 15/466,098, filed on Mar. 22, 2017, now Pat. No. 10,631,980.
(Continued)

(51) Int. Cl.
*A61F 2/24* (2006.01)
*A61M 25/01* (2006.01)
(Continued)

(52) U.S. Cl.
CPC ....... *A61F 2/2427* (2013.01); *A61M 25/0023* (2013.01); *A61M 25/0133* (2013.01);
(Continued)

(58) Field of Classification Search
CPC .......... A61F 2/2427; A61F 2/95; A61F 2/954; A61F 2/962; A61M 25/0133;
(Continued)

(56) References Cited

U.S. PATENT DOCUMENTS 5,332,402 A 7/1994 Teitelbaum
7,780,723 B2 8/2010 Taylor
(Continued)

FOREIGN PATENT DOCUMENTS

CN 2535048 Y 2/2003
CN 101708130 A 5/2010
(Continued)

OTHER PUBLICATIONS

PCT/US2017/023665, The International Search Report and the Written Opinion of the International Searching Authority, dated Jun. 26, 2017, 12 pgs.
(Continued)

*Primary Examiner* — Ryan J. Severson
*Assistant Examiner* — Andrew P. Restaino
(74) *Attorney, Agent, or Firm* — Medler Ferro Woodhouse & Mills PLLC

(57) ABSTRACT

An expandable introducer sheath provided with a steering mechanism is disclosed. The introducer sheath is configured for providing a prosthesis delivery system percutaneous access to a patient's vasculature. The introducer sheath includes a sheath component defining a central lumen and having a longitudinally-extending, radially-expandable portion. The sheath component also includes a steering wire slidably disposed within a wall thereof that longitudinally extends along the radially-expandable portion. When the steering wire is in a slackened configuration, the steering wire permits a width of the radially-expandable portion to increase. When the steering wire is in a taut configuration, the steering wire permits a distal portion of the sheath component to be manipulated or bent in order to align a distal port of the introducer sheath, for instance, with an ostium of a branch vessel.

13 Claims, 7 Drawing Sheets

Related U.S. Application Data

(60) Provisional application No. 62/315,782, filed on Mar. 31, 2016.

(51) Int. Cl.
  *A61M 25/00* (2006.01)
  *A61M 25/06* (2006.01)

(52) U.S. Cl.
  CPC ..... *A61M 25/0147* (2013.01); *A61M 25/0662* (2013.01); *A61M 2025/0024* (2013.01); *A61M 2025/0047* (2013.01); *A61M 2025/0059* (2013.01)

(58) Field of Classification Search
  CPC .......... A61M 25/0023; A61M 25/0662; A61M 25/0147; A61M 2025/0047; A61M 2025/0059; A61M 2025/0024; A61M 25/0051
  See application file for complete search history.

(56) References Cited

U.S. PATENT DOCUMENTS

| | | | |
|---|---|---|---|
| 8,491,650 | B2 | 7/2013 | Wiemeyer et al. |
| 8,568,472 | B2 | 10/2013 | Marchand et al. |
| 8,579,963 | B2 | 11/2013 | Tabor |
| 8,721,715 | B2 | 5/2014 | Wang |
| 8,747,459 | B2 | 6/2014 | Nguyen et al. |
| 8,790,387 | B2 * | 7/2014 | Nguyen ................ A61F 2/2427 623/1.11 |
| 9,956,376 | B2 * | 5/2018 | Anderson .......... A61M 25/0023 |
| 10,391,279 | B2 * | 8/2019 | Zhou ..................... A61F 2/2433 |
| 2004/0087968 | A1 | 5/2004 | Core |
| 2005/0203340 | A1 | 9/2005 | Butler et al. |
| 2009/0240202 | A1 | 9/2009 | Drasler et al. |
| 2010/0069834 | A1 | 3/2010 | Schultz |
| 2010/0198160 | A1 | 8/2010 | Voss |
| 2011/0260489 | A1 | 10/2011 | Zirkle et al. |
| 2012/0136339 | A1 | 5/2012 | Schlumpf |
| 2013/0282111 | A1 | 10/2013 | Dwork |
| 2014/0046343 | A1 | 2/2014 | Okazaki et al. |
| 2014/0052238 | A1 | 2/2014 | Wang et al. |
| 2014/0074227 | A1 | 3/2014 | Tabor |
| 2014/0121629 | A1 | 5/2014 | MaCaulay et al. |
| 2014/0188216 | A1 | 7/2014 | Bishop et al. |
| 2014/0236122 | A1 | 8/2014 | Anderson et al. |
| 2014/0236123 | A1 | 8/2014 | Birmingham et al. |
| 2014/0364939 | A1 | 12/2014 | Deshmukh et al. |
| 2015/0073539 | A1 | 3/2015 | Geiger et al. |
| 2015/0174363 | A1 | 6/2015 | Sutemeister et al. |
| 2015/0238178 | A1 * | 8/2015 | Carroux ............. A61B 1/00154 600/208 |
| 2016/0074067 | A1 * | 3/2016 | Furnish .............. A61B 17/3415 606/108 |

FOREIGN PATENT DOCUMENTS

| | | |
|---|---|---|
| CN | 202128807 U | 2/2012 |
| CN | 102548603 A | 7/2012 |
| CN | 103282074 A | 9/2013 |
| CN | 103491849 A | 1/2014 |
| CN | 104042376 A | 9/2014 |
| CN | 105358099 A | 2/2016 |
| WO | 2011/056311 A1 | 5/2011 |
| WO | 2012/061657 A2 | 5/2012 |
| WO | 2013136636 A1 | 9/2013 |
| WO | 2014066031 A1 | 5/2014 |

OTHER PUBLICATIONS

Office Action dated Nov. 3, 2020 in Chinese Appln No. 201780019747.3 (with English translation only), 9 pages.

* cited by examiner

EXPANDABLE INTRODUCER SHEATH

CROSS-REFERENCE TO RELATED APPLICATIONS

The present application is a continuation of prior U.S. application Ser. No. 15/466,098, filed Mar. 22, 2017, now U.S. Pat. No. [to be assigned], which claims the benefit of prior U.S. Appl. No. 62/315,782, filed Mar. 31, 2016, which are incorporated by reference herein in their entirety.

FIELD OF THE INVENTION

The present invention relates to an introducer sheath for providing a transcatheter valve prosthesis delivery system percutaneous access to a patient's vasculature, and, more particularly to an introducer sheath having an expandable section for accommodating passage of the transcatheter valve prosthesis delivery system therethrough.

BACKGROUND OF THE INVENTION

An introducer sheath provides percutaneous access to the vascular system of a patient and functions to permit the introduction and positioning of various minimally invasive medical devices within the patient's vasculature. Minimally invasive medical devices refer to inter alia any type of catheter sized to be introduced into the vasculature to include transcatheter valve prosthesis delivery systems. A conventional introducer sheath includes an elongate tubular component that defines a lumen of the introducer sheath, a hub component, and a hemostasis valve. It is known to commence a minimally invasive procedure within the vasculature by initially forming a percutaneous entry point via the Seldinger technique into a suitable vessel of the patient, such as a femoral, brachial, or radial artery. Thereafter, the elongate tubular component of the introducer sheath is partially inserted into the vasculature at the percutaneous entry point with a proximal port of the introducer sheath hub being accessible by a clinician so that minimally invasive medical devices may be introduced into and advanced through the lumen of the introducer sheath. In many minimally invasive procedures within the vasculature, a guidewire may first be inserted through the introducer sheath and subsequently advanced through the vasculature (and in certain applications another body structure) to a treatment site.

Recently minimally invasive approaches have been developed to facilitate catheter-based implantation of a valve prosthesis on a beating heart that are intended to obviate the need for the use of classical sternotomy and cardiopulmonary bypass. More particularly, flexible prosthetic valves supported by stent structures that can be delivered percutaneously using a catheter-based delivery system have been developed for heart valve replacement, and may be referred to herein as a transcatheter valve or a transcatheter heart valve prosthesis. Transcatheter heart valve prostheses may include either self-expanding or balloon-expandable stent structures with valve leaflets attached to the interior of the stent structure. They are configured to be reduced in diameter, by crimping onto a balloon catheter or by being contained within a sheath or outer tubular component of a delivery catheter, and thereafter advanced through the venous or arterial vasculature. Once the transcatheter heart valve prosthesis is positioned at the treatment site, for instance within an incompetent native valve or a previously implanted prosthetic heart valve, the frame or stent structure may be expanded to hold the prosthetic heart valve firmly in place.

The actual shape or configuration of any particular transcatheter heart valve prosthesis to be delivered in a transcatheter implantation procedure is dependent, at least to some extent, upon the native heart valve being replaced or repaired, i.e., mitral valve, tricuspid valve, aortic valve, or pulmonary valve. Most transcatheter heart valve prosthesis will have a relatively large delivery profile, as will at least a distal portion of a catheter-based delivery system within which the prosthesis is held in a compressed configuration. The use of such larger delivery profile catheter-based delivery systems, heretofore, required a larger diameter or sized introducer sheath in order to provide suitable clearance within the lumen thereof to allow the catheter-based delivery system to pass through the patient's vasculature. However, larger diameter or sized introducer sheaths may be suitable for use only in patients with sufficient vessel size to accommodate such an introducer sheath. In order to extend the availability of larger delivery profile transcatheter heart valve prostheses and their delivery systems to patients with smaller vessel sizes, expandable introducer sheaths with smaller diameters or sizes that are configured to locally expand within the patient's vasculature to allow passage of such prostheses and delivery systems are described in U.S. Patent Application Pub. No. 2014/0121629 to Macaulay et al. and U.S. Patent Application Pub. No. 2014/0236122 to Anderson et al., each of which is incorporated herein by reference in its entirety. Localized radial expansion and subsequent recoil of segments of the expandable introducer sheaths described in the Macaulay and Anderson publications may be less traumatic on the patient's vessel than sustained longitudinal and radial expansion of a fixed, larger diameter introducer sheath.

An expandable introducer sheath must be navigable through the vasculature, and, for certain procedures, it may be necessary for the clinician to accurately steer or deflect the introducer sheath so that a distal port or opening thereof may be aligned with an ostium of a branch or side vessel. It is known to employ a pull wire connected to a distal portion of certain catheters and controlled by a proximal handle component. With such mechanisms, when a wire is pulled, the catheter is deflected in the direction of the pulled wire. However, known pull wire mechanisms are insufficient and inadequate when it comes to accurately and controllably deflecting an expandable introducer sheath due to the longitudinally-extending radially-expandable sections of such introducer sheaths lacking sufficient stiffness or columnar strength to react in a reliable and/or uniform fashion in response thereto.

In light of the above, a need exists for an expandable introducer sheath having a steering mechanism that provides accurate, safe, and predictable deflection of the introducer sheath as it navigates the anatomy of the vasculature.

BRIEF SUMMARY OF THE INVENTION

In accordance with an aspect hereof, an introducer sheath for providing a prosthesis delivery system percutaneous access to a patient's vasculature is disclosed. The sheath includes a sheath component having a central lumen defined by a wall structure thereof, the wall structure being formed from a circumferentially continuous inner layer with a radially-expandable portion, and a circumferentially discontinuous outer layer that is connected to the circumferentially continuous inner layer, the circumferentially discontinuous outer layer including first and second longitudinally-extending edges between which the radially-expandable portion of the inner layer is defined. The radially-expandable portion of the circumferentially continuous inner layer of the wall structure is disposed inwardly of the first and second longitudinally-extending edges of the circumferentially discontinuous outer layer of the wall structure in each of an unexpanded state and an expanded state of the sheath component.

In accordance with another aspect hereof, an introducer sheath for providing a prosthesis delivery system percutaneous access to a patient's vasculature is disclosed. The sheath includes a sheath component having a wall structure formed from an inner liner with a radially-expandable portion, the radially-expandable portion having a first width when the sheath component is in an unexpanded state and a second width, greater than the first width, when the sheath component is in an expanded state, and an outer jacket that is connected to the inner liner, the outer jacket including first and second longitudinally-extending edges between which the radially-expandable portion of the inner liner extends. The radially-expandable portion of the inner liner of the wall structure is disposed inwardly of the first and second longitudinally-extending edges of the outer jacket of the wall structure in each of the unexpanded state and the expanded state of the sheath component.

BRIEF DESCRIPTION OF DRAWINGS

The foregoing and other features and advantages of the invention will be apparent from the following description of embodiments thereof as illustrated in the accompanying drawings. The accompanying drawings, which are incorporated herein and form a part of the specification, further serve to explain the principles of the invention and to enable a person skilled in the pertinent art to make and use the invention. The drawings are not to scale.

FIG. 2BB is a perspective view of an area B of the introducer sheath shown in FIG. 2 in accordance with another embodiment hereof with a wire structure of the sheath component exposed for illustrative purposes only.

DETAILED DESCRIPTION OF THE INVENTION

Specific embodiments of the present invention are now described with reference to the figures, wherein like reference numbers indicate identical or functionally similar elements. The terms "distal" and "proximal" are used in the following description with respect to a position or direction relative to the treating clinician. "Distal" or "distally" are a position distant from or in a direction away from the clinician. "Proximal" and "proximally" are a position near or in a direction toward the clinician. The following detailed description is merely exemplary in nature and is not intended to limit the invention or the application and uses of the invention. Although the description of the invention is in the context of treatment of heart valves, the invention may also be used where it is deemed useful in endoscopic procedures, procedures in the coronary vessels, or procedures in the peripheral vessels. Furthermore, there is no intention to be bound by any expressed or implied theory presented in the preceding technical field, background, brief summary or the following detailed description.

Figure 1:
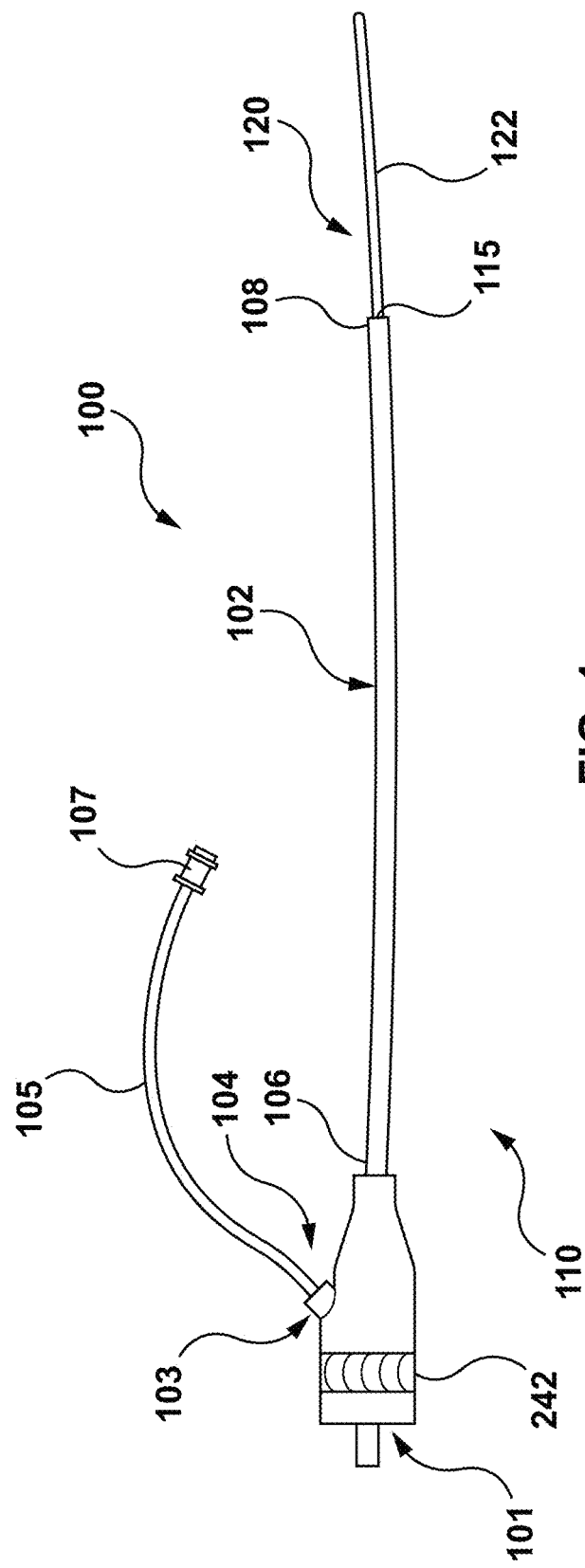
FIG. 1 depicts a side view of an introducer apparatus in accordance with an embodiment hereof.
Figure 2:
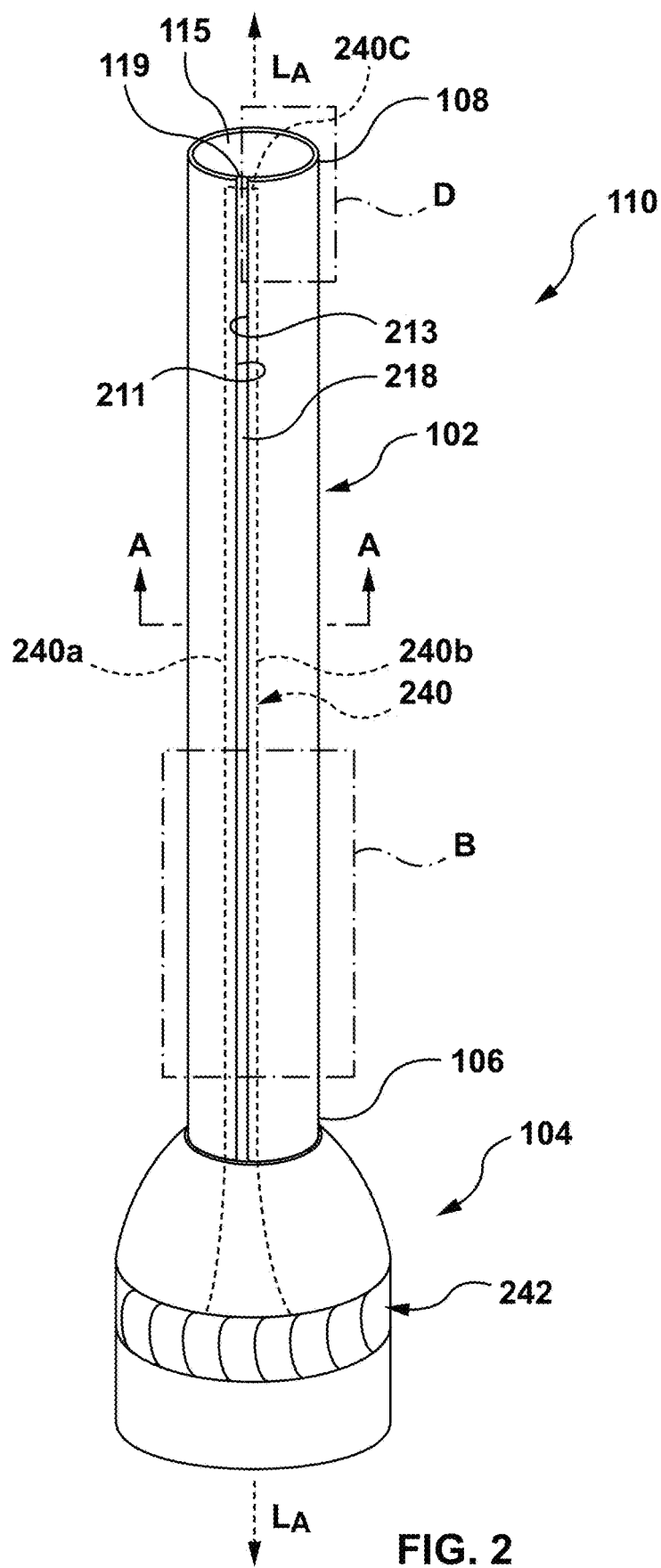
FIG. 2 depicts a side view of an introducer sheath in accordance with an embodiment hereof.
Figure 2A:
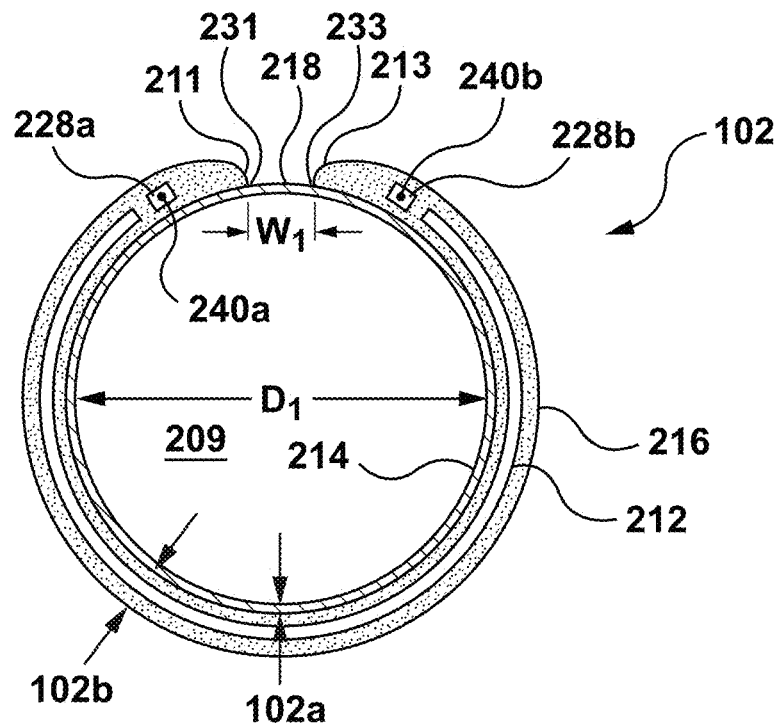
FIGS. 2A and 2AA are cross-sectional views of a sheath component of the introducer sheath of FIG. 2 taken at line A-A thereof, with FIG. 2A showing the sheath component in an unexpanded state and with FIG. 2AA showing the sheath component in an expanded state.
Figure 2A:
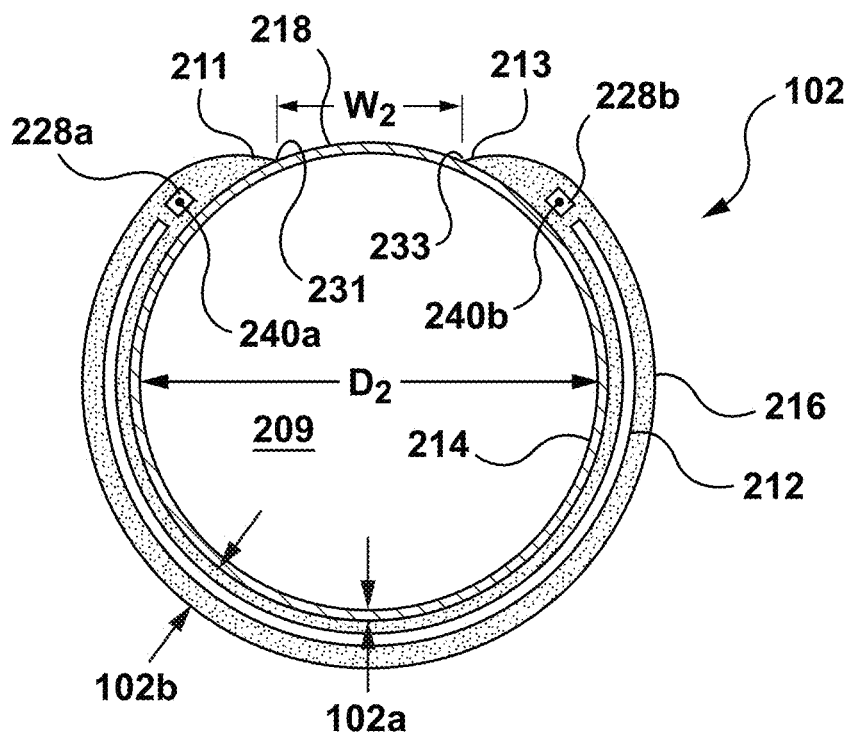

An introducer apparatus 100 in accordance with an embodiment hereof is shown in FIG. 1. Introducer apparatus 100 includes an introducer sheath 110 and a dilator 120. Introducer sheath 110 has a sheath component 102 and a handle component 104 attached at a proximal end 106 of the sheath component 102. With reference to FIGS. 2 and 2A, the sheath component 102 is a tubular structure that defines a central or interior lumen 209 from the proximal end 106 to a distal end 108 thereof, wherein the distal end 108 defines a distal port or opening 115 of the introducer sheath 110. The handle component 104 includes a hemostasis valve (not shown), a proximal port 101, and a side port 103. By way of example, but not limitation, in FIG. 1 a flush tube 105 having a Luer connector 107 is shown coupled to the side port 103 of the handle component 104. The dilator 120 is configured to slide through the introducer sheath 110, and more particularly is configured to be slidably disposed within the central lumen 209 of the sheath component 102 such that a distal portion 122 of the dilator 120 distally extends from the distal port 115 of the introducer sheath 110.

In order to track one or more minimally invasive medical device to a treatment site within a patient, such as to track a valve prosthesis delivery system to an incompetent heart valve of a patient, a clinician must first establish percutaneous access to a patient's vasculature. In a method of providing percutaneous access to a patient's vasculature in accordance herewith, which is presented by way of example, but not limitation, a puncture needle (not shown) may be inserted through the skin and into a vessel, such as one of a femoral, brachial, or radial artery. The puncture needle may then be slightly withdrawn until a flash of blood appears and thereafter a guidewire (not shown) may be inserted through the puncture needle and advanced into the vessel. With the guidewire in place, the introducer apparatus 100 may be advanced over the puncture needle such that the dilator 120 enlarges the access point into the vessel and the sheath component 102 of the introducer sheath 110 gains access to the vessel. Thereafter, the dilator 120 is removed, and the sheath component 102 of the introducer sheath 110 is left behind in the vessel holding the tract open and protecting the vessel from trauma as one or more minimally invasive medical devices are subsequently introduced into the vessel therethrough.

Figure 2B:
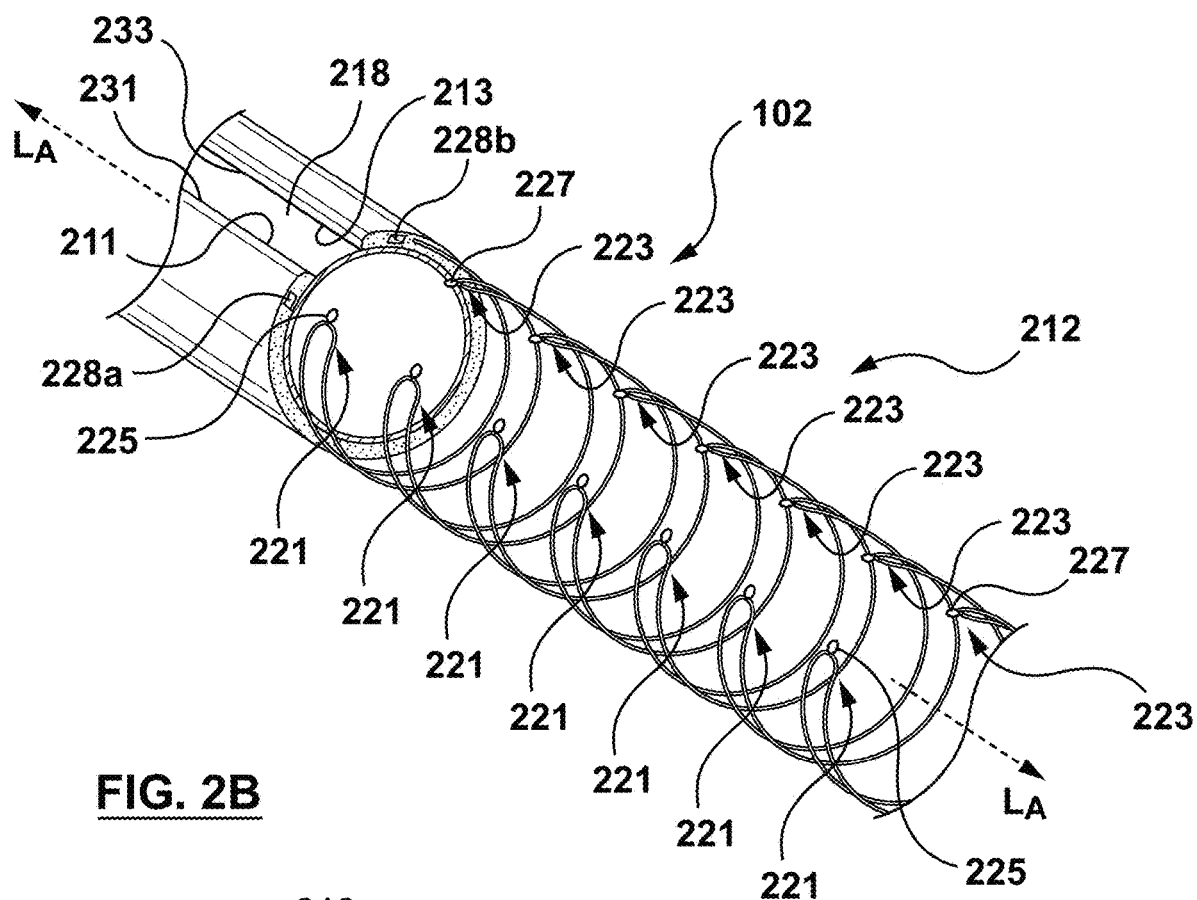
FIG. 2B is a perspective view of an area B of the introducer sheath shown in FIG. 2 in accordance with an embodiment hereof with a wire structure of the sheath component exposed for illustrative purposes only.
Figure 2B:
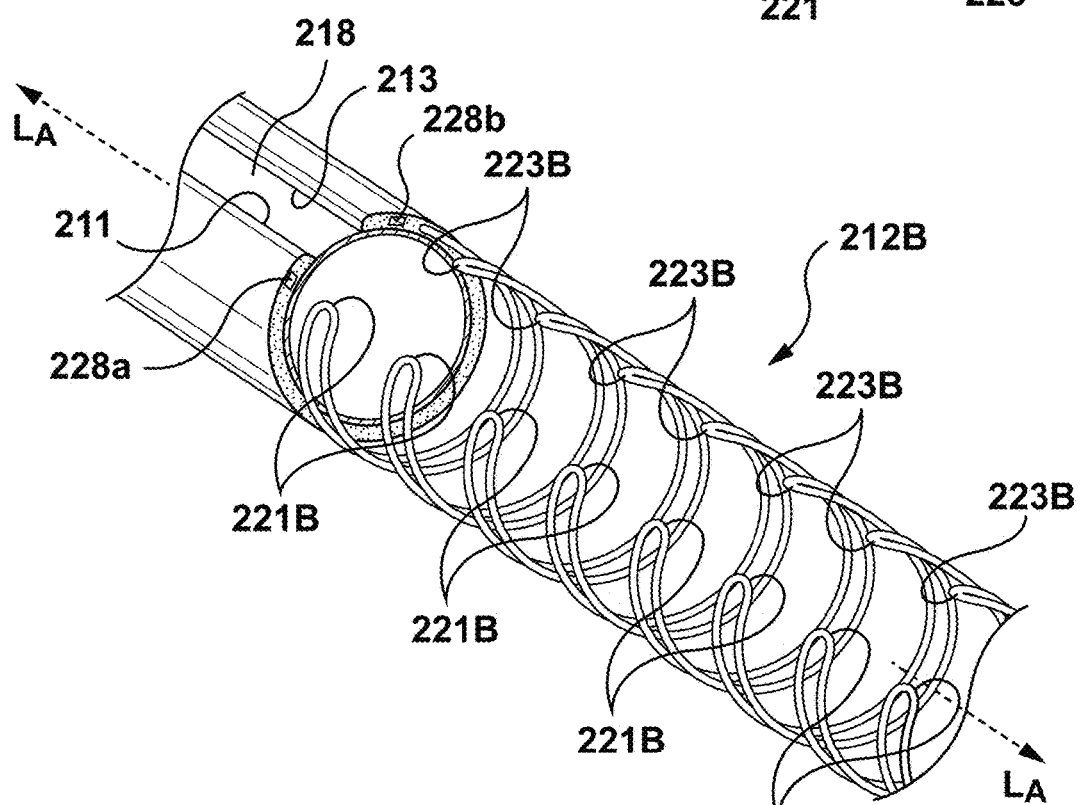

The introducer sheath 110 in accordance with embodiments hereof is described in more detail herein with reference to FIGS. 2, 2A, 2AA, 2B, 2BB 2C, 2D, 4 and 5. FIG. 2 is a side view of the introducer sheath 110 with the dilator 120 removed. Each of FIGS. 2A and 2AA is a cross-sectional view of the sheath component 102 of the introducer sheath 110 taken at line A-A in FIG. 2, with FIG. 2A showing the sheath component 102 in an unexpanded state and with FIG. 2AA showing the sheath component 102 in an expanded state. FIG. 2B is a perspective view of a segment B of the sheath component 102 shown in FIG. 2 with a wire structure 212 in accordance with an embodiment hereof exposed for illustrative purposes only. FIG. 2BB is a perspective view of an area B of the introducer sheath shown in FIG. 2 in accordance with another embodiment hereof with a wire structure 212B of a sheath component exposed for illustrative purposes only.

Referring to FIGS. 2A, 2AA and 2B, the sheath component 102 includes a wire structure 212, an inner liner 214, and an outer jacket 216 that are joined to each other to form a tubular wall of the sheath component. The inner liner 214 forms a circumferentially continuous inner layer 102a of the sheath component 102, whereas together the outer jacket 216 and the wire structure 212 may be considered to form a circumferentially discontinuous outer layer 102b of the sheath component 102, with the wire structure 212 providing kink resistance and reinforcement of the sheath component 102. In embodiments hereof, the inner layer 102a of the sheath component 102 (formed by the inner liner 214) defines a longitudinally-extending, radially-expandable portion 218 between first and second longitudinally-extending edges 211, 213 of the outer layer 102b of the sheath component 102 (formed by the outer jacket 216 and the wire structure 212). In embodiments hereof, a sheath component may be described as having a longitudinally-extending, radially-expandable portion, such as expandable portion 218, disposed between a reinforced portion, such as a remainder of the sheath component 102 formed from at least the circumferentially discontinuous outer layer 102b of the outer jacket 216 and the wire structure 212.

In embodiments hereof, an inner liner may be formed from tetrafluoroethylene (TFE), Teflon®, polytetrafluoroethylene (PTFE), polyethylene, polyethylene terephthalate (PET), or polyester. In an embodiment hereof, an inner liner may have a low coefficient of friction on its inner surface to facilitate advancement of one or more minimally invasive medical devices through an introducer sheath in accordance with embodiments hereof. In embodiments hereof, an outer jacket may be formed from a polyurethane (e.g. Pellethane®, Elasthane™, Texin®, or Tecothane®) and can include 20% barium sulfate added as a radiopacifier. In other embodiments, an outer jacket may be formed from a polyamide polyether block copolymer, such as Pebax®, nylon 12, or polyethylene. In other embodiments, an outer jacket may be loaded with tungsten or bismuth subcarbonate to add radiopacity so that an introducer sheath in accordance with embodiments hereof may be radio detectable (radiopaque).

In embodiments hereof, a wire structure may be formed of a shape memory material such as a nickel titanium alloy (nitinol), with a diameter of the wire ranging, for e.g., from approximately 0.005 inches to approximately 0.02 inches. In other embodiments, a wire structure may be formed of a resilient material, such as a nickel-cobalt-chromium-molybdenum alloy (MP35N), stainless steel, high spring temper steel, or any other metal or composite having elastic properties to permit radial expansion and recoil of an introducer sheath in accordance with embodiments hereof.

Figure 3:
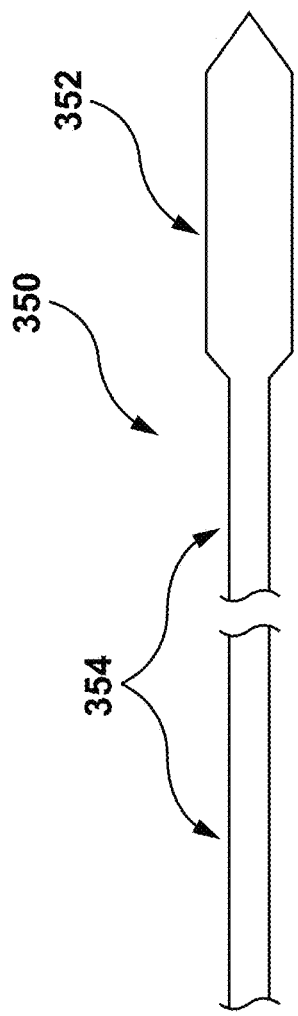
FIG. 3 depicts an exemplary distal portion of a valve prosthesis delivery system for use with an introducer sheath in accordance herewith.
Figure 4:
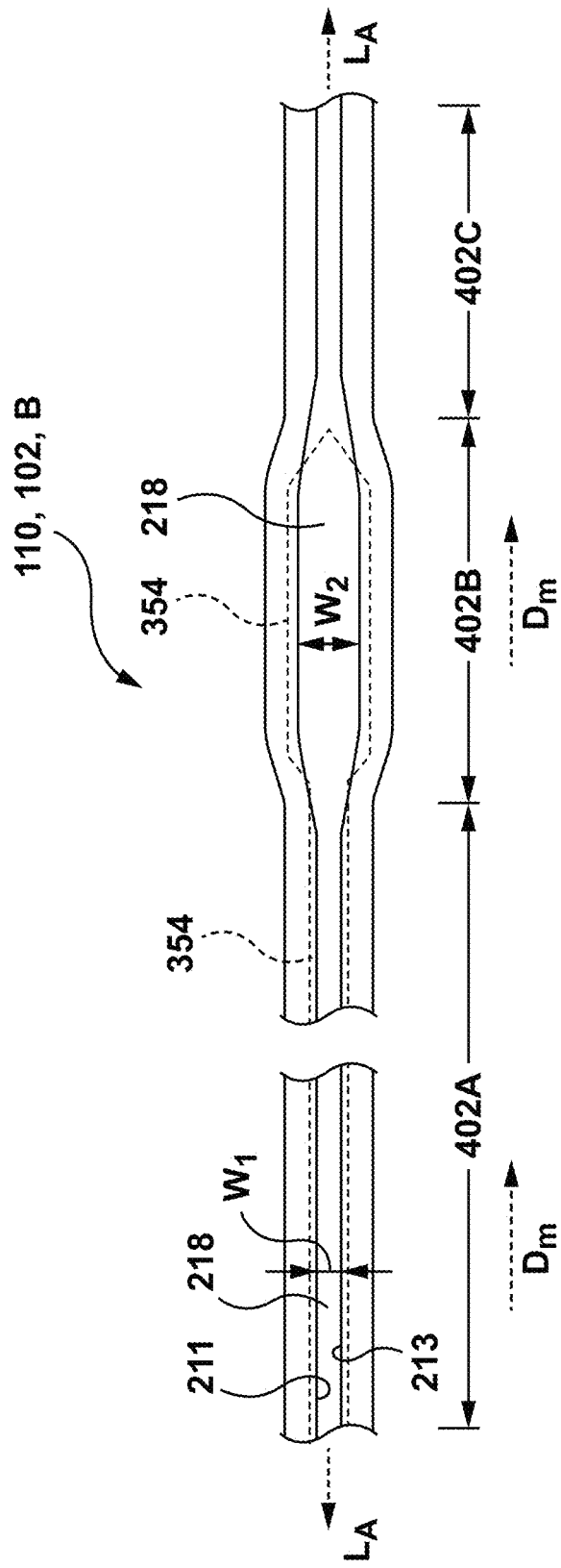
FIG. 4 depicts the distal portion of the valve prosthesis delivery system of FIG. 3 positioned within the segment B of the introducer sheath of FIG. 2.

In an embodiment hereof, the wire structure 212 of the outer layer 102b of the sheath component 102 is formed from a shape memory or resilient material to actively recoil or return the radially-expandable portion 218 of the sheath component 102 to its original, unexpanded state (as represented by the cross-section shown in FIG. 2A) after passage therethrough of a valve prosthesis delivery system. In order to illustrate this functionality, FIG. 3 depicts an exemplary distal portion of a valve prosthesis delivery system 350 that includes a distal segment or capsule 352 within which a transcatheter heart valve prosthesis (not shown) may be held in a compressed delivery configuration, and FIG. 4 depicts the distal segment 352 being distally advanced within the segment B of the introducer sheath 110. Due to the relatively larger delivery profile of a compressed heart valve prosthesis, the distal segment 352 of the valve prosthesis delivery system 350 has a delivery profile (or outer diameter) that is wider or larger than a delivery profile (or outer diameter) of a remaining proximal segment 354 of the valve prosthesis delivery system 350. In accordance with embodiments hereof, the introducer sheath 110 is configured to radially expand as the distal segment 352 of the valve prosthesis delivery system 350 is distally advanced or pushed therethrough, wherein the dashed arrows in FIG. 4 are intended to represent the distal movement $D_M$ of the valve prosthesis delivery system 350 relative to the introducer sheath 110.

More particularly with reference to FIGS. 2A, 2AA, 3 and 4, the radially-expandable portion 218 of the sheath component 102 of the introducer sheath 110 is configured to locally and temporarily expand or stretch from a width $W_1$ to a width $W_2$ to transition or expand an area or segment 402B of the sheath component 102 within which the distal segment 352 of the valve prosthesis delivery system 350 is positioned as it is distally advanced relative to the introducer sheath 110. When the radially-expandable portion 218 of the sheath component 102 is at the width $W_1$, the central lumen 209 of the sheath component 102 has a reduced, first inner diameter $D_1$ in all unexpanded areas or segments 402A, 402C (see FIGS. 2A and 4). When the radially-expandable portion 218 of the sheath component 102 is transitioned to the width $W_2$ due to the distal segment 352 being disposed therein, the central lumen 209 of the sheath component 102 has an expanded, second diameter $D_2$ in the expanded area or segment 402B (see FIGS. 2AA and 4). It should be evident from this description that the expanded area or segment 402B changes longitudinal position along the sheath component 102 to correspond with the continued distal advancement of the distal segment 352 through (and relative to) the introducer sheath 110, such that the positions of segments 402A, 402B, 402C shown in FIG. 4 are intended to be illustrative and not limiting in any way.

By way of example and not limitation heart valve prosthesis delivery systems suitable for use with an introducer sheath in accordance with embodiments hereof are described in further detail in U.S. Pat. Appl. Pub. No. 2014/0364939 to Deshmukh et al., U.S. Pat. No. 8,562,673 to Yeung et al., U.S. Pat. No. 8,579,963 to Tabor, U.S. Pat. No. 8,974,524 to Yeung et al., U.S. Pat. No. 8,998,980 to Shipley et al., and U.S. Pat. No. 9,149,358 to Tabor et al., each of which is incorporated by reference herein in its entirety.

With reference to FIGS. 2A and 2B, the wire structure 212 curves or bends around a longitudinal axis $L_A$ of the sheath component 102 into a C-shaped configuration with first and second series of curved portions 221, 223 of the wire structure 212 aligning with respective first and second longitudinally-extending edges 211, 213 of the outer layer 102b of the sheath component 102. In an embodiment hereof by way of illustration and not limitation, each of a series of curved portion 221, 223 has a respective eyelet 225, 227 formed on or secured thereto such that the wire structure 212 may also be considered to define or include first and second series of eyelets 225, 227 that align with respective first and second longitudinally-extending edges 211, 213 of the outer layer 102b. In other embodiments, every other or every third curved portion 221, 223 may have a respective eyelet 225, 227 formed thereon without departing from the scope hereof. In still other embodiments, only one or more consecutive or non-consecutive curved portions 221, 223 located along a distalmost portion of the sheath component 102 may have a respective eyelet 225, 227 formed thereon without departing from the scope hereof. When the inner and outer layers 102a, 102b are bonded to each other during formation of the sheath component 102, at least the first and second series of eyelets 225, 227 of the wire structure 212 are disposed within respective longitudinally-extending channels or pockets 228a, 228b formed within the outer layer 102b. The longitudinally-extending channels 228a, 228b extend within the outer layer 102b substantially in parallel with respective first and second longitudinally-extending edges 211, 213 of the outer layer 102b, as well as substantially in parallel with respective first and second longitudinally-extending sides 231, 233 of the radially-expandable portion 218. The first and second sides 231, 233 may be also be described herein as opposing sides 231, 233 of the radially-expandable portion 218.

In another embodiment with reference to FIGS. 2A and 2BB, first and second series of curved portions 221B, 223B of the wire structure 212B aligning with respective first and second longitudinally-extending edges 211, 213 of the outer layer 102b of the sheath component 102 do not include eyelets. In such an embodiment when the inner and outer layers 102a, 102b are bonded to each other during formation of the sheath component 102, at least the first and second series of curved portions 221B, 223B of the wire structure 212B are disposed within respective longitudinally-extending channels 228a, 228b formed within the outer layer 102b.

With reference to one or more of the prior described figures, a steering mechanism that provides accurate, safe, and predictable deflection of the sheath component 102 of the introducer sheath 110 will now be described. The steering mechanism includes a steering wire 240 that is operably coupled to a rotatable knob 242 of the handle component 104. Broadly described, the steering wire 240 extends from the handle component 104 to the distal end 108 of the sheath component 102 and is slidably disposed therebetween within the longitudinally-extending channels 228a, 228b formed within the outer layer 102b of the sheath component 102. The steering wire 240 may be described as having a first segment 240a slidably disposed within the longitudinally-extending channel 228a of the outer layer 102b, and longitudinally extending essentially in parallel with the first side 231 of the expandable portion 218 between the distal end 108 of the sheath component 102 and the handle component 104. Similarly, the steering wire 240 may be described as having a second segment 240b slidably disposed within the longitudinally-extending channel 228b of the outer layer 102b, and longitudinally extending essentially in parallel with the second side 233 of the expandable portion 218 between the distal end 108 of the sheath component 102 and the handle component 104. In embodiments in accordance herewith, the steering wire 240 may also include a lateral segment 240c defined or extending between respective distal ends of the first and second segments 240a, 240b, wherein at least a portion of the lateral segment 240c is slidably disposed within the expandable portion 218 of the sheath component 102 proximal of a distal end 119 of the expandable portion 218. As used herein with reference to the first and second segments 240a, 240b of the steering wire 240 "slidably" denotes back and forth movement in a longitudinal direction along the longitudinal axis $L_A$ of the introducer sheath 110, and as used herein with reference to the lateral segment 240c of the steering wire 240 "slidably" denotes back and forth movement in a substantially transverse direction relative to the longitudinal axis $L_A$ of the introducer sheath 110.

Figure 2C:
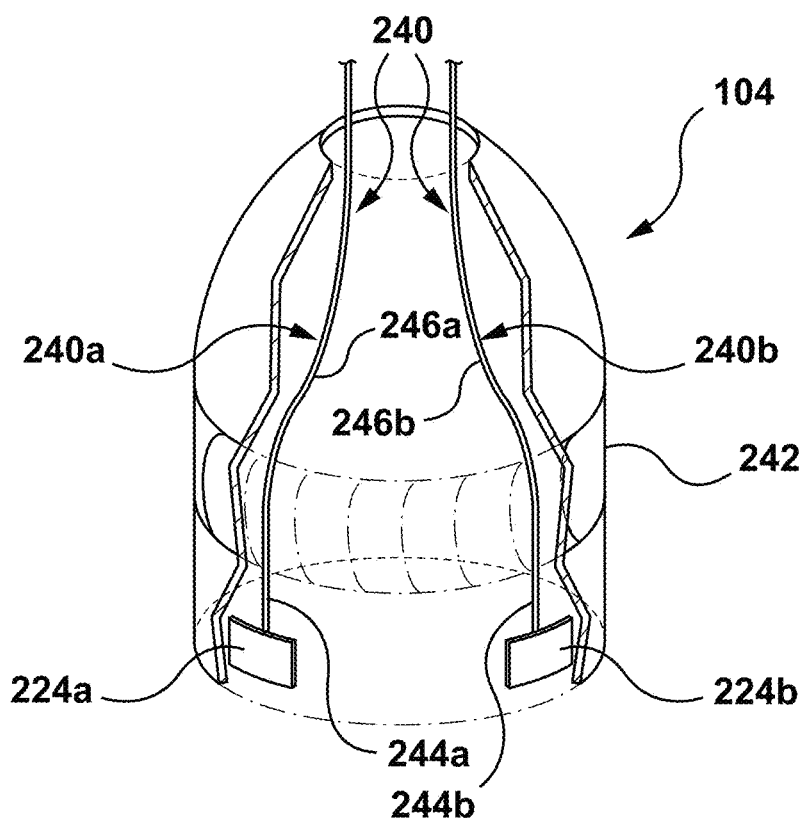
FIG. 2C depicts a cut away view of a handle component in accordance with an embodiment hereof.
Figure 2D:
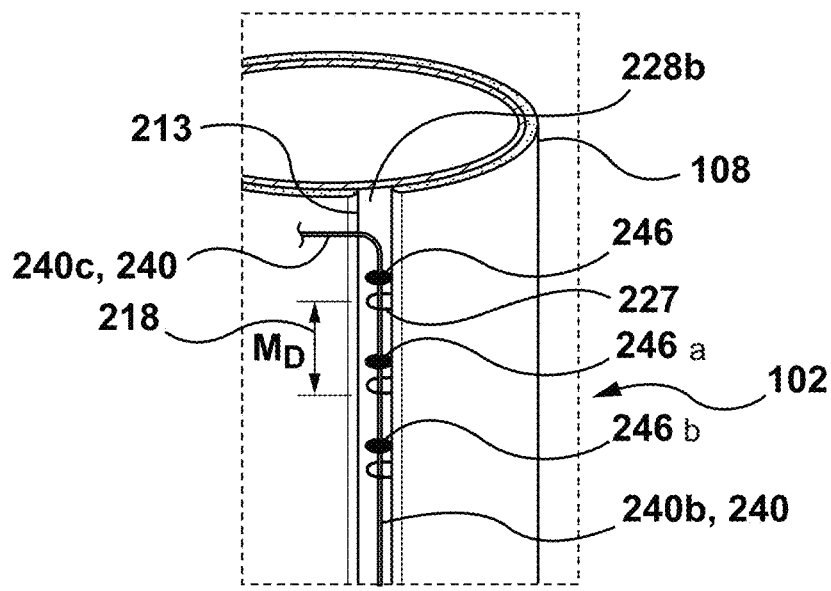
FIG. 2D depicts a partial sectional view of an area D of the introducer sheath shown in FIG. 2.

FIG. 2D depicts a partial sectional view of an area D in FIG. 2 of the sheath component 102 with a distalmost portion of the channel 228b laid open for illustrative purposes. In embodiments in accordance herewith, the second segment 240b of the steering wire 240 may slidably extend or pass through one or more of the second series of eyelets 227 (or one or more of the second series of curved portions 223) that lie within the channel 228b particularly along the distalmost portion of the sheath component 102, as shown in FIG. 2D. Similarly although not shown in detail, the first segment 240a of the steering wire 240 may slidably extend or pass through one or more of the first series of eyelets 225 (or one or more of the first series of curved portions 221) that lie within the channel 228a, particularly along a distalmost portion of the sheath component 102. In accordance with embodiments hereof, at least the distalmost portions of the first and second segments 240a, 240b of the steering wire 240 include one or more stops, bumps or protrusions 246 that are disposed distal of a corresponding eyelet 225, 227 (or curved portion 221, 223). The stops 246 are sized to be larger than an opening of the corresponding eyelet 225, 227 (or curved portion 221, 223), as shown in FIG. 2D for the distalmost portion of the second segment 240b.

The spatial relationship between the stops 246 and eyelets 225, 227 (or curved portions 221/223) is provided to permit limited distal movement of the first and second segments 240a, 240b of the steering wire 240 relative to the eyelets 225, 227 (or curved portion 221, 223) in a distal direction to thereby allow expansion of the expandable portion 218. Stated more particularly with reference to FIG. 2D, stops 246a, 246b are each disposed between a respective proximal and distal eyelet 227 and each stop 246a, 246b may be distally advanced up to a distance MD by the sliding movement of the second segment 240b of the steering wire 240 before the second segment 240b of the steering wire 240 is prevented from further distal movement by contact being made by the stops 246a, 246b with its respective distal eyelet 227.

In addition, when the stops 246 engage with their corresponding proximal eyelets 225, 227 (or curved portions 221/223) as the first and second segments 240a, 240b of the steering wire 240 are proximally pulled or tensioned the interaction between the stops and distal sides or ends of the eyelets/curved portions functions to return or maintain the expandable portion 218 in an unexpanded state, such as during tracking of the sheath component within the vasculature. With continued tensioning of the first and second segments 240a, 240b of the steering wire 240 in a proximal direction, a distal portion 502 of the sheath component 102 may be bent or deflected into the deflected or curved state shown in FIG. 5 by a corresponding bending force being applied by the stops 246 against the distal sides or ends of their corresponding eyelets or curved portions.

In embodiments in accordance herewith, the first, second and lateral segments 240a, 240b, 240c of the steering wire 240 may be formed by a single wire. In other embodiments hereof, the first, second and/or lateral segments 240a, 240b, 240c of the steering wire 240 may be formed by more than one wire joined together. In still other embodiments, a first segment 240a and a second segment 240b of a steering wire 240 may be individual and separate wires and no lateral segment may be disposed therebetween. Steering wires in accordance with embodiments hereof may be formed from one or more wires of a suitable stainless steel, Nitinol, UHMWPE (Ultra High Molecular Weight Polyethylene), and Nylon.

FIG. 2C depicts a cut away view of the handle component 104 showing proximal ends 244a, 244b of the steering wire 240 fixed within an interior of the handle component 104 at locations 224a, 224b therein such that proximalmost portions 246a, 246b of the first and second segments 240a, 240b of the steering wire 240 are disposed within the interior of the handle component 104. In addition, the proximalmost portions 246a, 246b of the first and second segments 240a, 240b are operably coupled to the rotatable knob 242 such that when the rotatable knob 242 is turned or rotated in a first direction the proximalmost portions 246a, 246b are wound or turned about a feature of the knob to transition the steering wire 240 into a taut configuration. When the steering wire 240 is in a taut configuration, the first and second segments 240a, 240b are tensioned in a proximal direction, and when sufficient tensioning or force is applied to the sheath component 102 via the interaction between the stops 246 of the steering wire 240 and the eyelets/curved portions of the wire structure 212 deflection or bending of the distal portion 502 of the sheath component 102 will occur.

Figure 5:
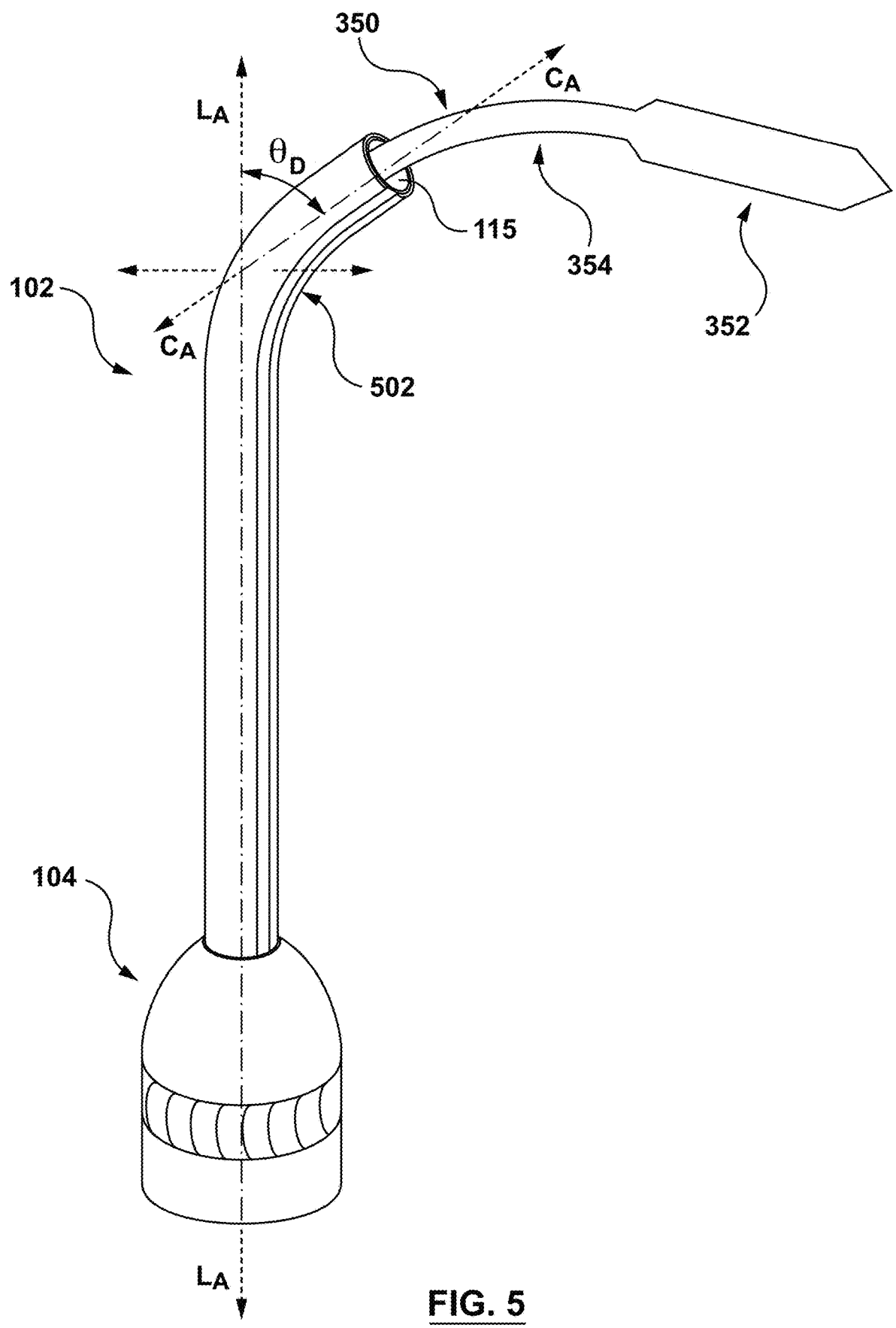
FIG. 5 depicts a side view of an introducer apparatus 100 in accordance with an embodiment hereof after being steered into a deflected state with the distal portion of the valve prosthesis delivery system of FIG. 3 distally extending therefrom.

In embodiments hereof, the amount of rotation of the knob 242 in the first direction may be selected depending on a desired degree of deflection $\Theta_D$, as determined by radiographic imaging or other suitable imaging within the vasculature of the distal end 108 of the sheath component 102. In embodiments hereof, a degree of deflection $\Theta_D$ is measured between the longitudinal axis $L_A$ of the sheath component 102 in a straightened, undeflected state, as shown in FIG. 1, and a central axis $C_A$ of the deflected distal portion 502 of the sheath component 102, as shown in FIG. 5. By way of example and not limitation, a quarter turn of the knob 242 may correspond to an approximately 15° deflection, a half turn of the knob 242 may correspond to an approximately 30° deflection and/or a three quarter turn of the knob 242 may correspond to an approximately 45° degree deflection. In an embodiment, the rotatable knob 242 may be provided with markings to indicate when the knob has been turned in the first direction to a position that corresponds with the sheath component 102 being deflected to a certain angle of deflection, such as by way of example and not limitation, a series of markings with each marking corresponding to a deflection of the sheath component 102 to a respective one of 10°, 15°, 20°, 25°, etc. In an embodiment, the rotatable knob 242 may also have a locked or delivery position at which the steering wire 240 is sufficiently taut to prevent the radially-expandable portion 218 of the sheath component 102 from expanding and/or to aid in returning the radially-expandable portion 218 to an unexpanded state. In an embodiment in a locked position, the sheath component 102 may be fixed in a deflected state. In another embodiment, when the rotatable knob 242 is turned or rotated in a second direction (opposite of the first direction) the proximalmost portions 246a, 246b are unwound from about the feature of the knob to transition the steering wire 240 into a slackened or loosened configuration. In an embodiment, the overall length of the steering wire 240 is such that in the slackened configuration the steering wire 240 permits a width of the radially-expandable portion 218 of the sheath component 102 to increase or widen sufficiently to permit the passage of the valve prosthesis delivery system 350 as described above.

In order to track one or more minimally invasive medical device to a treatment site within a patient, such as to track a valve prosthesis delivery system to an incompetent heart valve of a patient, a clinician must first establish percutaneous access to a patient's vasculature. In a method of providing percutaneous access to a patient's vasculature in accordance herewith, which is presented by way of example, but not limitation, a puncture needle (not shown) may be inserted through the skin and into a vessel, such as one of a femoral, brachial, or radial artery. The puncture needle may then be slightly withdrawn until a flash of blood appears and thereafter a guidewire (not shown) may be inserted through the puncture needle and advanced into the vessel. With the guidewire in place, the introducer apparatus 100 may be advanced over the puncture needle such that the dilator 120 enlarges the access point into the vessel and the sheath component 102 of the introducer sheath 110 gains access to the vessel. Thereafter, the dilator 120 is removed, and the sheath component 102 of the introducer sheath 110 is left behind in the vessel holding the tract open and protecting the vessel from trauma as one or more minimally invasive medical devices are subsequently introduced into the vessel through.

In order to align the distal port 115 of the introducer sheath 110 with an ostium of a branch or side vessel, the rotatable knob 242 may be rotated to sufficiently tension the steering wire 240 to bend the distal portion 502 of the sheath component 102 (as described above) to align the distal port 115 with the ostium.

While various embodiments have been described above, it should be understood that they have been presented only as illustrations and examples of the present invention, and not by way of limitation. It will be apparent to persons skilled in the relevant art that various changes in form and detail can be made therein without departing from the spirit and scope of the invention. Thus, the breadth and scope of the present invention should not be limited by any of the above-described exemplary embodiments, but should be defined only in accordance with the appended claims and their equivalents. It will also be understood that each feature of each embodiment discussed herein, and of each reference cited herein, can be used in combination with the features of any other embodiment. All patents and publications discussed herein are incorporated by reference herein in their entirety.

What is claimed is:
1. An introducer sheath for providing a prosthesis delivery system percutaneous access to a patient's vasculature, the sheath comprising:
a sheath component having a central lumen defined by a wall structure thereof, the wall structure formed from
a circumferentially continuous inner layer with a radially-expandable portion, and
a circumferentially discontinuous outermost layer that is connected to the circumferentially continuous inner layer, the circumferentially discontinuous outermost layer including first and second longitudinally-extending edges between which the radially-expandable portion of the inner layer is defined; and a C-shaped wire structure embedded within the circumferentially discontinuous outermost layer of the wall structure for providing kink resistance and reinforcement to the sheath component, wherein the radially-expandable portion of the circumferentially continuous inner layer is disposed inwardly of the first and second longitudinally-extending edges of the circumferentially discontinuous outermost layer in each of an unexpanded state of the sheath component in which no portion of the sheath component is expanded and an expanded state of the sheath component, and wherein in both the unexpanded state and the expanded state of the sheath component the first and second longitudinally-extending edges of the circumferentially discontinuous outermost layer are non-overlapping.

2. The introducer sheath of claim 1, wherein a first distance is defined between the first and second longitudinally-extending edges of the circumferentially discontinuous outermost layer of the wall structure when the sheath component is in the unexpanded state, and wherein a second distance, greater than the first distance, is defined between the first and second longitudinally-extending edges of the circumferentially discontinuous outermost layer of the wall structure when the sheath component is in the expanded state.

3. The introducer sheath of claim 1, wherein the radially-expandable portion of the circumferentially continuous inner layer of the wall structure has a first width when the sheath component is in the unexpanded state, and wherein the radially-expandable portion of the circumferentially continuous inner layer of the wall structure has a second width, greater than the first width, when the sheath component is in the expanded state.

4. The introducer sheath of claim 3, wherein the central lumen of the sheath component has a first diameter when the radially-expandable portion of the circumferentially continuous inner layer of the wall structure has the first width, and wherein the central lumen of the sheath component has a second diameter, greater than the first diameter, when the radially-expandable portion of the circumferentially continuous inner layer of the wall structure has the second width.

5. The introducer sheath of claim 4, wherein the central lumen of the sheath component expands from the first diameter to the second diameter when at least a distal portion of the prosthesis delivery system is passed therethrough.

6. The introducer sheath of claim 1, wherein the C-shaped wire structure is formed from a shape-memory or resilient material to return the sheath component from the expanded state to the unexpanded state.

7. An introducer sheath for providing a prosthesis delivery system percutaneous access to a patient's vasculature comprising:

a sheath component having a wall structure formed from
an inner liner with a radially-expandable portion, the radially-expandable portion having a first width when the sheath component is in an unexpanded state and a second width, greater than the first width, when the sheath component is in an expanded state, wherein the first width is a smallest width of the radially-expandable portion, and an outermost jacket that is connected to the inner liner, the outermost jacket including first and second longitudinally-extending edges between which the radially-expandable portion of the inner liner extends; and a C-shaped wire structure embedded within the outermost jacket of the wall structure for providing kink resistance and reinforcement to the sheath component, wherein the radially-expandable portion of the inner liner is disposed inwardly of the first and second longitudinally-extending edges of the outermost jacket in each of the unexpanded state and the expanded state of the sheath component; and wherein in both the unexpanded state and the expanded state of the sheath component the first and second longitudinally-extending edges of the outermost jacket are non-overlapping.

8. The introducer sheath of claim 7, wherein a central lumen of the sheath component has a first diameter when the radially-expandable portion of the inner liner of the wall structure has the first width, and wherein the central lumen of the sheath component has a second diameter, greater than the first diameter, when the radially-expandable portion of the inner liner of the wall structure has the second width.

9. The introducer sheath of claim 8, wherein the central lumen of the sheath component expands from the first diameter to the second diameter when at least a distal portion of the prosthesis delivery system is passed therethrough.

10. The introducer sheath of claim 7, wherein a first distance is defined between the first and second longitudinally-extending edges of the outermost jacket of the wall structure when the sheath component is in the unexpanded state, and wherein a second distance, greater than the first distance, is defined between the first and second longitudinally-extending edges of the outermost jacket of the wall structure when the sheath component is in the expanded state.

11. The introducer sheath of claim 7, wherein the C-shaped wire structure is formed from a shape-memory or resilient material to return the sheath component from the expanded state to the unexpanded state.

12. The introducer sheath of claim 7, wherein the inner liner forms a circumferentially continuous inner layer.

13. The introducer sheath of claim 12, wherein the outermost jacket forms a circumferentially discontinuous outermost layer.

* * * * *